United States Patent [19]

Clark, Jr.

[11] Patent Number: 4,467,811

[45] Date of Patent: Aug. 28, 1984

[54] METHOD OF POLAROGRAPHIC ANALYSIS OF LACTIC ACID AND LACTATE

[75] Inventor: Leland C. Clark, Jr., Cincinnati, Ohio

[73] Assignee: Children's Hospital Medical Center, Cincinnati, Ohio

[21] Appl. No.: 346,951

[22] Filed: Feb. 8, 1982

Related U.S. Application Data

[63] Continuation-in-part of Ser. No. 63,159, Aug. 2, 1979, Pat. No. 4,401,122.

[51] Int. Cl.³ .............................................. A61B 5/00
[52] U.S. Cl. .................................. 128/635; 204/1 T; 204/403; 128/637
[58] Field of Search ................ 128/635, 637; 204/1 T, 204/1 R, 138, 160.1, 401–403

[56] References Cited

U.S. PATENT DOCUMENTS

| | | |
|---|---|---|
| 3,795,239 | 3/1974 | Eberhard et al. .................... 128/635 |
| 4,129,478 | 12/1978 | Racine et al. ........................ 204/403 |
| 4,230,122 | 10/1980 | Lübbers et al. ..................... 128/635 |
| 4,240,438 | 12/1980 | Updike et al. ....................... 128/635 |
| 4,259,963 | 4/1981 | Huch .................................... 128/635 |
| 4,353,983 | 10/1982 | Siddigi ................................. 204/403 |

Primary Examiner—Benjamin R. Padgett
Assistant Examiner—T. J. Wallen
Attorney, Agent, or Firm—Wood, Herron & Evans

[57] ABSTRACT

A method of measuring lactic acid or lactate and derivatives thereof in liquids which is extremely versatile and is suitable for use in a number of areas such as the rapid measurement of lactic acid in whole blood, the ratio of lactic acid to pyruvic acid in whole blood, in-vivo measurement of lactic acid and the study of living lactic acid-producing cells. The acid or lactate is measured by reacting the lactic acid with lactic oxidase to produce pyruvate and $H_2O_2$. The $H_2O_2$ is then measured polarographically. The current produced is directly proportional to the lactate level. Preferably, the lactic oxidase is trapped between two semi-permeable membranes. One membrane is placed in contact with an electrolyte at the tip of an electrode and the second membrane contacts the liquid being tested.

7 Claims, 4 Drawing Figures

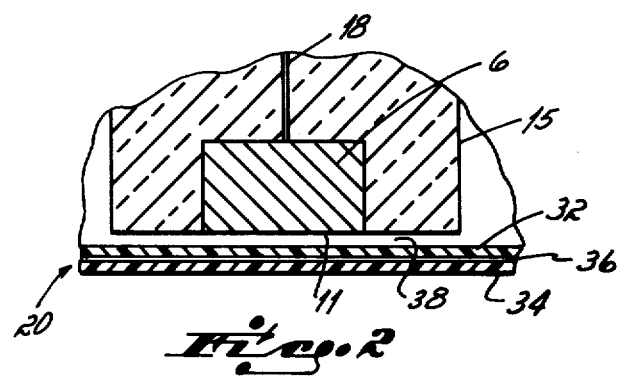

METHOD OF POLAROGRAPHIC ANALYSIS OF LACTIC ACID AND LACTATE

RELATED APPLICATION

The present application is a continuation in part of application Ser. No. 63,159, filed Aug. 2, 1979, now U.S. Pat. No. 4,401,122.

BACKGROUND OF THE INVENTION

The present invention is a continuation-in-part of an application entitled Cutaneous Methods of Measuring Body Substances, Ser. No. 63,159, filed Aug. 2, 1979 which is now pending. This application disclosed the concept of analyzing lactate by reacting lactate with lactic oxidase to produce hydrogen peroxide. The hydrogen peroxide was then measured polarographically using a cutaneous electrode. The present invention deals with the problem of rapidly measuring lactic acid or lactate in whole mammalian blood.

Medical science is now realizing the importance of rapidly measuring lactic acid levels in blood, skeletal muscles and the heart. Lactic acid levels in blood appears to be an indication of certain critical features in mammals. A high blood lactic acid level frequently is an indication that a mammal is about to go into shock. For accident victims, it could be extremely critical to rapidly determine the lactic acid level. Such a determination should be rapid and use minute quantities of blood in order to permit repeated measurements of lactic acid level. In infants, lactic acid levels are important indicators of defects in metabolism of carbohydrates. With infants, sample sze is extremely critical since the amount of blood in the infant is substantially less than that of an adult.

Some authorities theorize that the ratio of lactic acid to pyruvic acid in blood is important. Accordingly, any method of measuring lactic acid should preferably also enable one to measure pyruvic acid in order to determine this ratio.

Currently, there are various methods to measure lactic acid. When the lactic acid is measured in whole blood, the plasma generally must be separated from the blood to eliminate undesirable substances which could cause side reactions. For example, the lactic acid has been measured indirectly by reduction using a lactic dehydrogenase which consumes oxygen and the oxygen decrease is thereby measured to indicate lactic acid levels. This is an indirect measurement of lactic acid and tends to be extremely expensive and time consuming. In these reactions, the blood is separated from the lactic dehydrogenase by using a semi-permeable membrane. Other methods include colorimetric methods in which the blood plasma is separated from the whole blood cells using filtration or centrifugation to separate the whole blood cells from the plasma. The plasma can then be reacted with lactic oxidase to produce hydrogen peroxide which can be colorimetrically measured. These methods are time consuming and expensive and fail to provide a means to rapidly detect lactic acid directly.

Furthermore, these methods fail to provide a means to measure the ratio of lactic acid to pyruvic acid and further fail in that they do not provide a means to measure in situ lactic acid levels. This would be particularly important in measuring lactic acid levels in the heart.

About 15 years ago, enzyme-coupled electrodes were reported for the polarographic analysis of the substances. For example, my U.S. Pat. No. 3,539,455 discloses a membrane polarographic electrode system method for the rapid and accurate quantitative analysis of substances which theretofor posed difficulties in analyzing directly by polarographic methods. According to the description in my mentioned patent, small molecular substances, such as glucose, were measured with a membrane polarographic electrode system. By use of cellulose or another membrane which is permeable to small molecules such as glucose, but impermeable to proteins, the membrane keeps glucose oxidase enzyme on the side of the membrane with the anode for reaction with glucose. Therefore, for example, when a sample of blood were placed on the membrane side opposite the electrode with an aqueous solution of enzyme and oxygen on the electrode side of the membrane, low molecular weight molecules such as glucose pass from the blood samples through the membrane for enzymatic reaction adjacent the electrode. After a certain period of time, a steady state is reached when the hydrogen peroxide concentration is directly proportional to the glucose concentration and the cell produces a current flow as a function of the amount of hydrogen peroxide being formed which serves as an indication of the amount of glucose present.

Lactic oxidase for some time has been puzzling the scientific world. For some time, it was a matter of dispute whether lactic oxidase, in fact, could produce hydrogen peroxide from lactic acid. One possible reason for this dispute is frequently the enzyme had associated therewith a substantial amount of a catalase which would quickly consume hydrogen peroxide. A second source of this dispute was the improper characterization of lactic oxidase. Certain enzymes, which were actually lactic oxoreductases, were characterized as lactic oxidases. These lactic oxoreductases, instead of producing hydrogen peroxide and pyruvate from lactic acid, produced acetic acid, carbon dioxide and water. However, it has been recently appreciated in the literature that there are true lactic oxidases and which are substantially catalase free and suitable for the reaction to produce hydrogen peroxide from lactic acid or lactate. Such an enzyme is disclosed in U.S. Pat. No. 4,166,763, assigned to Eastman Kodak Company. This patent discloses an enzyme for use in analysis of lactic acid whereby the lactic acid is oxidized to produce pyruvate and hydrogen peroxide. The hydrogen peroxide is measured colorimetrically.

SUMMARY OF THE INVENTION

The present invention is premised upon the realization that lactic oxidase could be used to oxidize lactate or lactic acid to produce pyruvate and hydrogen peroxide and the hydrogen peroxide could thereby be measured polarographically. Particularly, it has been found that lactic acid can migrate through a membrane into contact with lactic oxidase where it is converted to hydrogen peroxide. The produced hydrogen peroxide will then migrate through a second membrane to an electrode. The decomposition of the hydrogen peroxide will produce a current flow across the cell which can be determined as a measure of rate of formation of the hydrogen peroxide and is an indication of the amount of lactic acid or lactate present in the material under analysis.

A number of advantages are provided by this invention. Lactic acid can be measured directly even when the lactic acid is contained in whole blood which may contain a great deal of catalase. In this situation, the sample does not have to be prepared prior to analysis to eliminate any unwanted contaminants. Thus, a measurement of lactic acid level can be made in about 40 seconds.

In one of its broader aspects, this invention is directed to a method of quantitative polarographic determination of lactic acid which is converted by at least one enzyme to produce hydrogen peroxide. A polarographic cell is provided, including at least one electrode sensitive to hydrogen peroxide. A sensing electrode is positioned behind a first membrane which is permeable to hydrogen peroxide. Lactic oxidase and potentially additional enzymes are contained between this first membrane and a second membrane which separates the enzyme from the sample. Lactic acid in the sample migrates through the second membrane to react with the lactic oxidase and produce hydrogen peroxide and pyruvate. The hydrogen peroxide then passes through the first membrane into the electroltye of the cell. Potential is established across the cell and the produced current is proportional to the amount of hydrogen peroxide produced.

In such a membrane polarographic cell, a quantity of material containing lactic acid to be measured is added for enzymatic reaction on the side of the membrane opposite the electrode and to effect diffusion of at least a portion of the hydrogen peroxide into the membrane and into contact with the electrode. Then the current flowing across the cell is determined as a function of the amount of hydrogen peroxide formed and as an indication of the amount of the lactic acid in the material. The current flow is measured as the rate of formation of hydrogen peroxide by enzymatic reaction with the lactic acid. In the modifications of the present invention, pyruvic oxidase is admixed with the lactic oxidase to react with the formed pyruvate. The pyruvate in the presence of pyruvic oxidase forms acetic acid and hydrogen peroxide. Thus, more hydrogen peroxide is produced from the same amount of lactic acid. This substantially increases the sensitivity of the detection of lactic acid.

Polarographic cells of this type can be modified to measure the ratio of lactic acid to pyruvic acid. Furthermore, these cells can be added to catheters to measure in-vivo lactic acid levels. These cells can also be modified by immobilization of various animal, plant or bacterial cells which produce lactic acid onto the outer membranes. This provides a method of observing lactic acid production by these cells. This heretofor unappreciated versatility of such a method of measuring lactic acid is an extremely critical advantage of the present invention.

The invention will be further understood and its advantages appreciated with reference to the following detailed descriptions and drawings in which:

FIG. 2 is an enlarged view of the lower central portion of the polarographic cell of FIG. 1 and showing in more detail the laminated membrane of the polarographic cell.

Throughout the specification, the term lactic acid and lactate may be used interchangeably. The present method provides a means to measure lactate, lactic acid as well as lactic acid derivatives which react with lactic oxidase to produce hydrogen peroxide. These derivatives include phenyl lactate and ethyl lactate. The method of the present invention is premised on the following reaction.

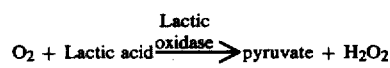

Figure 1:
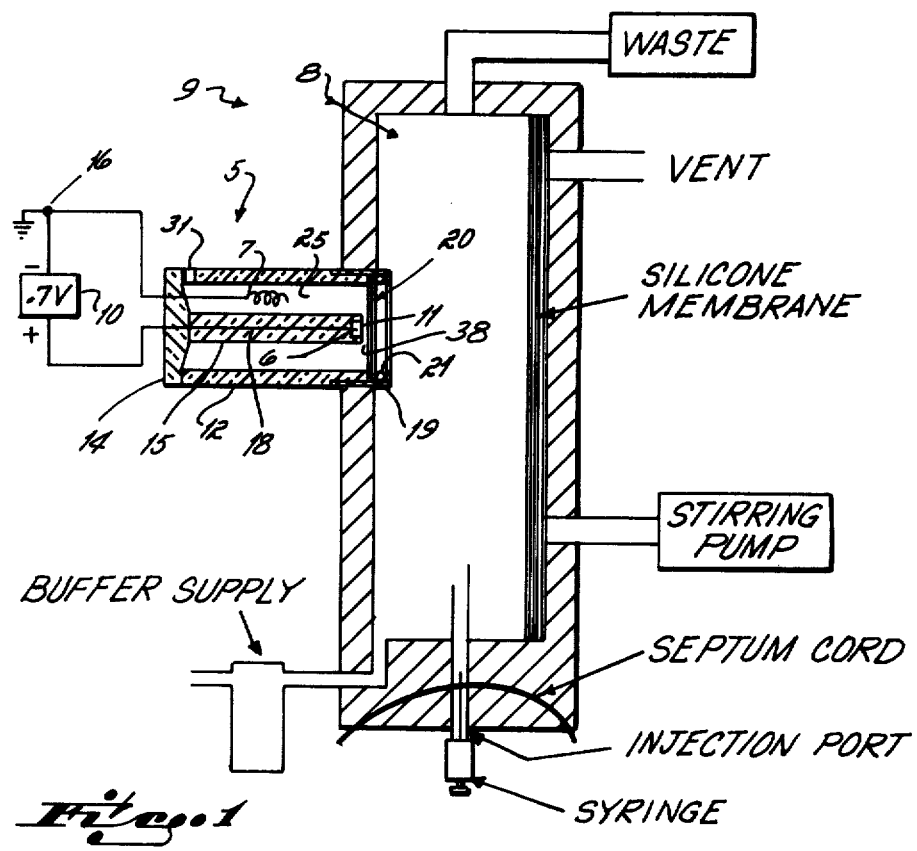
FIG. 1 is a diagrammatic illustration of a polarographic instrument and other means employed in the methods of this invention showing the overall arrangement of an electrical circuit, polarographic cells, and the sample chamber.

The hydrogen peroxide is then measured using a membrane polarographic cell of the type shown in FIGS. 1 and 2 and more particularly, disclosed in my patent, U.S. Pat. No. 3,539,455 which is incorporated herein by reference.

In the polarographic apparatus of FIG. 1, the electrode probe 5 oxidizes a constant portion of the hydrogen peroxide at the platinum anode 6 as most probably illustrated by the following reaction.

$$H_2O_2 + 2H^+ \rightarrow O_2 + 2e^-$$

The circuit is completed by silver cathode 7 at which oxygen is reduced to water as most probably illustrated by the following reaction.

$$4H^+ + O_2 \rightarrow 2H_2O - 4e^-$$

Relating the above reactions to the principle of operation in FIG. 1 of the drawing, FIG. 1 is a diagrammatic illustration of an apparatus illustrating the polarographic cell 9 with electrode probe 5 and sample chamber 8.

In the detailed operation which follows, a modified Model 23, Yellow Springs Instrument Company Glucose Analyzer was employed and is here described as follows. The cell is provided with its own potential source which in this case is a battery 10 using an applied voltage of about 0.7 volts. The positive pole of the battery is attached to the platinum polarographic anode 6 having a face 11 diameter of 0.5 mm with an adjacent silver chloride coated silver wire reference cathode 7 having an active surface area of about 0.5 square cm. A full scale output is of the order magnitude of 100 nanoamperes. A G-2500 varian strip chart recorder (not shown) was used to make the current measurements. Referring to FIG. 1, there is shown a cell assembly which includes an electrically insulating support body 12 of plastic or glass which is preferably cylindrical and which is covered by an electrically insulating cap 14. Positioned within a cylindrical body 12 is an electrically insulating member rod 15 of plastic or glass which supports a platinum electrode, the latter, including an active exposed face 11. The electrode 6 is attached to a battery source 10 by a conductor 18 which passes through rod 15 and through cap 14.

The lower end of the support body 12 is provided with an annular ring or retainer 19 and a laminated membrane 20. This laminated membrane is supported over the end of the supporting body nearest the electrode 6 and spaced a capillary distance from the active face 11. The membrane is held in position on the supporting body by an O-ring 21.

An annular space is provided between the rod 15 and the supporting body 12 and receives a reference electrode 7 which may be, for example, silver chloride coated silver wire. The space 25 between rod 15 and supporting body 12 is at least partly and preferably completely filled with a liquid mixture of electrolyte which contains both electrodes 7 and 6 and which may be introduced in the chamber through an aperture 31 provided beneath the cap 14. Typical electrolytes include sodium or potassium chloride buffers including carbonate, phosphate, bicarbonate, acetates, or alkali or rare earth metals or other organic buffers for mixtures thereof. The solvent for such electrolyte may be water, glycols, glycerine and mixtures thereof. In the present invention, an aqueous mixture of $Na_2HPO_4$ and $NaH_2PO_4$ is preferably used.

FIG. 2 shows membrane 20 more fully and will be referred to primarily in the description of that membrane. Layer 32 as shown is that adjacent the active surface 11 of anode 6. That layer is essentially homogenous silicone, methyl, methacrylate or cellulose acetate material. Layer 34 is the outer layer which will be in contact with the sample to be analyzed. In the preferred embodiment, this is a 0.03 micron pore size perforated polycarbonate film having a thickness of 5 microns, nitrogen flow rate of 25 ml/min/cm$^2$ at the 10 psi and having six$\times 10^8$ holes per centimeter square. Such films are available from the Nuclepore Filtration Products of Pleasanton, Calif. When an approximately 5-7 micron thick support film is used, the overall thickness of the laminated membrane is less than 10 microns as is preferred. Typical thickness would be 5 microns for outer layer 34. One micron for inner layer 32 and one micron for the intermediate enzyme layer 36 for a total of 7 microns thickness. Layer 36 is the enzyme material used to react with the lactic acid and/or pyruvate and acts to bond layers 32 and 34 together.

Laminate membrane 20 is preferably produced by first placing the essentially homogeneous layer on a strippable carrier sheet. In the case of cellulose acetate, this is done by depositing the cellulose acetate in a solvent, cyclohexanone, for example, onto water. A film forms which can be picked up by a strippable carrier sheet, such as polyethylene. A similar process can be used for silicones and other essentially homogeneous material, such as methyl methacrylate. As mentioned, the preferred thickness for the essentially homogeneous layer is in the range of 0.5 to 1.0 microns.

The lactic oxidase preparation may be simply a mixture of lactic oxidase in water. Of course, other materials, such as a binder or a cross linking agent like gluteraldehyde may be included in the enzyme preparation. Likewise, the portion of lactic oxidase to water in the preparation is not material as long as a flowable paste or solution is formed which may be coated or pressed easily into a thin uniform layer, and sufficient enzyme is incorporated by an adequate reactive amount of measurements. About 17-20 U of enzyme provides sufficient enzyme activity to test 10 to 25 $\mu$sample having up to about 200 mg/ml lactic acid. The enzyme solution is further discussed below.

After placing the aqueous enzyme solution or paste onto the essentially homogeneous layer, a self sustaining support sheet of diffusion barrier material 34, preferably a porous polycarbonate is brought into contact with the enzyme preparation on the cellulose acetate layer to form a laminate. The laminate is then dried by allowing it to sit in air at room temperature for a half hour or more. Additionally, to condition the laminate for transit and storage, it may be baked at 45° C. for approximately half an hour. When the carrier sheet is removed, the laminate membranes are ready for installation onto a polarographic cell.

However, if preferred, the laminating procedure may be followed by gluing onto the support layer 34, a rubbery O-ring 21 of an appropriate size for fitting into the retainer 19 on the polarographic cell 10 (see FIG. 1). Laminated membranes 20 ready for use may be punched around the O-rings. Of course, the support layer is stripped off the face of the essentially homogeneous layer in this case also.

Most significantly, because the laminated membranes may be less than 10 microns in thickness, less than 30 seconds, and in some cases, as few as 10 seconds is taken for a polarographic analysis. During that short period of time, the lactic acid and oxygen diffuse through the layer 34, react with the lactic oxidase in layer 36. Then the hydrogen peroxide formed diffuses through layer 32 to contact the active face 11 of the anode 6. The current reaches a steady state and the measurement of the amount of hydrogen peroxide is made. This quick measurement time is extremely important in laboratories and hospitals for numerous analysis must be made each day. The membrane structure as described above is more fully described in U.S. Pat. Nos. 3,979,274 and 4,073,713 which are both incorporated herein by reference.

Positioned at the side of the sample chamber 8 is a thin oxygen-permeable membrane such as silicon rubber which permits the passage of air or oxygen from a stirring pump into the enzyme electrolyte mixture contained in the sample chamber 8 and the gas is eliminated through the vent. A syringe for injection of a sample is shown with buffer supply, injection port, septum cord and waste removal, thereby illustrating flow of sample analysis.

Critical for the present invention is the use of a proper lactic oxidase capable of catalyzing the reaction of proper lactic acid or lactate to form hydrogen peroxide and pyruvate. The lactic oxidase must be substantially catalase-free. Catalase is an enzyme which quickly binds and destroys hydrogen peroxide. Therefore, if substantial quantities of catalase are present, the hydrogen peroxide is consumed prior to reaching the active face of the electrode. Thus, the electrode will not detect any hydrogen peroxide. Therefore, the enzyme should be catalase-free.

The enzyme furthermore, should be water soluble to enable the passage of aqueous solutions of lactic acid into the enzyme. There are several sources of the lactic oxidase. H. J. Eichel and L. T. Roehm in the *Journal of Biochemistry*, 237, 940–945 (1962) disclosed a bacterium *Tetrahymen pyreformis* which produces a lactic oxidase which oxidizes lactate to pyruvate and hydrogen peroxide. F. B. Cousins, in the *Journal of Biochemistry*, 64, 297–307 (1956) reports a lactic oxidase which produces pyruvate and hydrogen peroxide from lactic acid derived from *Myco smegmatis* bacterium. Finally, U.S. Pat. No. 4,166,763 discloses a lactic oxidase obtained from *Streptococcus faecalis* (atcc 12755) which oxidizes lactic acid or lactate to form pyruvate and hydrogen peroxide. A commercial source of the enzyme is Fermco Biochemicals Inc. which sells a lactic oxidase which is believed to be made by Pedioccus Sp. This is the preferred enzyme. Its catalytic activity may be increased by the addition of flavin adenine dinucleotide (FAD) which is believed to be a coenzyme. As describe above in the discussion of the membrane laminate 20, the selected lactic oxidase is incorporated in the membrane structure of the polarographic cell.

In operation, the membrane polarographic instrument of FIG. 1 is used for the quantitative determination of lactic acid or a lactate derivative which is convertible by lactic oxidase to produce hydrogen peroxide. Aqueous electrolyte and buffer solution is introduced into the sample chamber 8. The lactic oxidase is included in the membrane laminate 20. The sample under analysis is introduced into chamber 8 by means of a syringe through the septum cord. Oxygen is provided by the stirring pump through the permeable silicone rubber membrane into the vented sample chamber. As the lactic acid in the sample comes into contact with the outer membrane layer 34, lactic acid is allowed to diffuse through the membrane layer into the enzyme layer 36. Catalase which may be contained in certain samples such as human blood is prevented from passage through the membrane layer 34 due to the small pore size of layer 34. The lactic acid or lactate derivative which passes into the enzyme layer is oxidized to produce hydrogen peroxide which is allowed to migrate through the inner membrane layer 32. This hydrogen peroxide passes across the capillary space 38 between the active face of the anode 11 and the inner membrane layer 32 and causes a current flow. This current flow across the cell is directly proportional to the quantity of hydrogen peroxide diffusing through layers 32. The determination of the current flowing across the cell by the galvanometer 16 is a function of the amount of hydrogen peroxide formed and is an indication of the amount of lactic acid or lactate in the sample. This measurement is a kinetic measurement. Initially, the current is low, but as shown in FIG. 4, the current quickly increases and after about 10 to 30 seconds, levels out. At this point, the production of hydrogen peroxide reaches a steady rate which is proportional to the amount of hydrogen peroxide produced. Comparing this current with a calibration curve made using known quantities of lactate as shown in FIG. 3 provides the lactic acid level in the sample.

The optimum operating conditions will vary depending on the sample and the source of the enzyme. However, it has been found using the Fermco lactic oxidase that a temperature of about 37° C. should be used with a pH of between 6 to 8.

Figure 3:
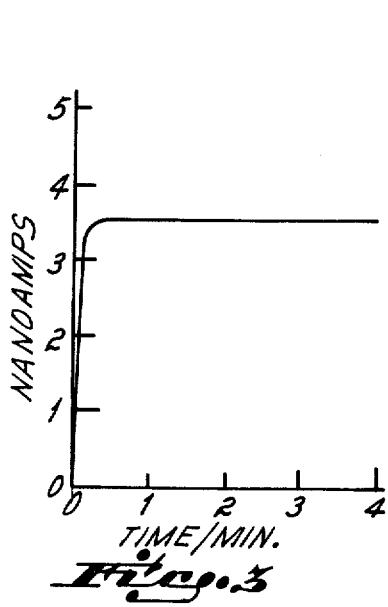
FIG. 3 is a typical calibration curve made according to the method of the present invention.
Figure 4:
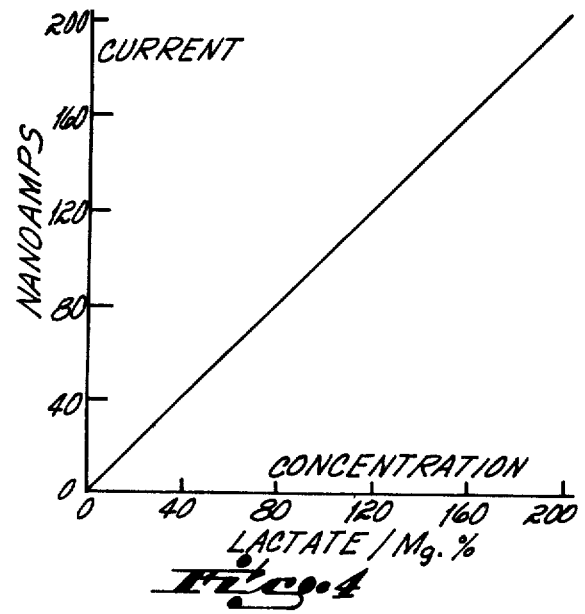
FIG. 4 is a plot of current versus time for a whole blood sample.

The results shown in both FIG. 3 and FIG. 4 were obtained using Fermco lactic oxidse without added FAD. The buffer was an aqueous mixture of $Na_2HPO_4$ and $NaH_2PO_4$ with a pH of 7.28. The temperature was 37° C. The sample sizes was 25 ul which was injected into a 350 ul cuvet. Using these conditions, linearity is excellent from 0–300 mg/dl of lactate. As stated previously, the life of the enzyme may be increased by adding small amounts of FAD to the buffer.

Optionally, pyruvate oxidase can be added to the enzyme layer of the membrane laminate 20 to cause the pyruvate which is produced from the lactic acid to be oxidized to produce hydrogen peroxide and acetic acid. This is demonstrated in the following equation;

Suitable sources of pyruvate oxidase is the enzyme produced by Pediococcus Sp. (EC1.2.3.3.) described in *Analytica Chemica Acta* 118 (1980) 65-71. Preferably, in this application, equimolar amounts of pyruvate oxidase and lactate oxidase are used in the enzyme layer. The laminate membrane is prepared just as described above with the only exception that the pyruvate oxidase is added. Thus, according to this method, the following reactions take place.

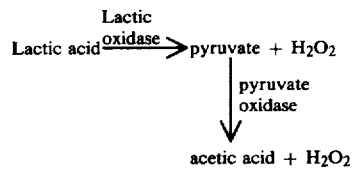

Theoretically, according to this scheme, twice as much hydrogen peroxide is produced from the same amount of lactic acid. This quantitatively increases the amount of hydrogen peroxide produced. Therefore, according to this method, lower amounts of lactic acid or lactate can be detected. It should be noted that this method is not as precise if the sample contains pyruvate.

Medical science has recently considered the importance of the ratio of lactic acid and the pyruvic acid in human blood. This is considered by some to be an important indicator of impending shock. Using the previously described method of measuring lactic acid, one can also determine the ratio of lactic acid to pyruvic acid in blood. This modified method is accomplished by using the same previously described method of detecting lactic acid using human whole blood as the sample. After the lactic acid in the human whole blood is measured, lactic dehydrogenase and NADH are injected into the cuvet of the electrode to react with the pyruvic acid in the blood sample. The pyruvic acid reacts with LDH and NADH to produce lactic acid. Accordingly, the lactic acid level will increase and the current flow will also increase. This increase in current will be caused by the lactic acid derived from pyruvic acid in the blood. Thus, by comparing the initial reading showing lactic acid level in the blood and the second reading showing the increase caused by pyruvic acid in the blood, one can determine the ratio of lactic acid to pyruvic acid. This mechanism of producing lactic acid from pyruvic acid is discussed in *Analytica Chemica Acta* 118 (1980), 65-7. Thus, according to the present method, one cannot only determine the lactic acid in the blood, but the level of pyruvic acid in the blood.

A further use of the method of the present invention is for the observation and study of certain cells which produce lactate. It is known to immobilize a bacteria or other cell in the end of an electrode using glyceraldehyde. The glyceraldehyde and the bacteria are mixed together and physically coated onto the tip of the electrode. Using the method of the present invention, one can place upon the end of the electrode a bacterium such as *Lactus Bacillus acidophilus*. This bacteria is used to produce lactic acid and is important in the dairy industry. By measuring the lactic acid produced under various conditions, one can study the bacterium more closely and the effect of various environments on the bacteria. Other cells which are known to create lactic acid are liver cells and leukemia cells. These also may be studied according to the method.

In addition to this use, the method of the present invention can also be used to measure lactic acid levels in vivo. It is known that a malfunctioning heart sometimes produces lactic acid. Accordingly, by attaching an electrode similar to probe 5 to the tip of a catheter, one can directly measure lactic acid level in the heart.

Thus, according to the above-described method, one can polarographically directly measure the amount of lactic acid contained in whole mammalian blood or in numerous other types of samples. The present method enables one to increase the sensitivity of the measurement by incorporating pyruvic oxidase with the lactic oxidase. The method of the present invention also provides a quick inexpensive method to detect a ratio of lactic acid to pyruvic acid, for example, in mammalian blood. This method also provides a means to study cells which produce lactic acid as well as measure in vitro lactic acid levels. Thus, this method is extremely versatile, much more versatile than prior art methods well as being less expensive and quicker.

Having thus described my invention, I claim:

1. The method of measuring lactic acid or derivatives thereof in a liquid and subsequently measuring pyruvate in said liquid comprising reacting said lactic acid or said derivatives thereof with lactic oxidase to produce pyruvate and hydrogen peroxide and measuring said hydrogen peroxide polarographically; and contacting said pyruvate with pyruvate oxidase, thereby producing acetic acid and hydrogen peroxide and measuring the produced hydrogen peroxide polarographically.

2. A method of measuring the ratio of lactic acid or derivatives thereof to pyruvic acid or derivatives thereof in a liquid comprising measuring the lactic acid in said liquid by reacting said lactic acid or derivative thereof with lactic oxidase, thereby producing hydrogen peroxide and pyruvate and measuring said hydrogen peroxide polarographically, and further comprising converting pyruvic acid in said liquid to lactic acid and subsequently measuring the lactic acid in said blood.

3. The method claimed in claim 2 wherein said liquid is whole mammalian blood.

4. The method claimed in claim 2 wherein said lactic oxidase is trapped between an inner and an outer membrane layer wherein said outer membrane layer separates said liquid from said enzyme and allows lactic acid or derivatives thereof to pass therethrough, and said inner membrane separates said enzyme from an electrolyte and allows hydrogen peroxide to pass therethrough.

5. The method claimed in claim 4 wherein said anode is separated from said inner membrane by a capillary layer of electrolyte.

6. The method claimed in claim 2 wherein said pyruvic acid in said liquid is converted to lactic acid by adding NADH and lactic dehydrogenase to said liquid.

7. A method of measuring the ratio of lactic acid or derivatives thereof to pyruvic acid or derivatives thereof in whole mammalian blood comprising measuring the lactic acid in said blood by reacting said lactic acid or derivatives thereof with lactic oxidase to produce pyruvate and hydrogen peroxide and measuring the hydrogen peroxide polarographically; and adding NADH and lactic dehydrogenase to said blood, thereby converting pyruvic acid or derivatives thereof in said blood to lactic acid and subsequently reacting the lactic acid with lactic oxidase to produce hydrogen peroxide and measuring the hydrogen peroxide polarographically.

* * * * *